United States Patent
Zimmermann et al.

(10) Patent No.: US 7,544,799 B2
(45) Date of Patent: *Jun. 9, 2009

(54) CRYSTAL MODIFICATION OF A N-PHENYL-2-PYRIMIDINEAMINE DERIVATIVE, PROCESSES FOR ITS MANUFACTURE AND ITS USE

(75) Inventors: Jürg Zimmermann, Basel (CH); Bertrand Sutter, Hesingue (FR); Hans M Bürger, Allschwil (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/515,997

(22) Filed: Sep. 5, 2006

(65) Prior Publication Data

US 2007/0004746 A1    Jan. 4, 2007

Related U.S. Application Data

(63) Continuation of application No. 11/241,266, filed on Sep. 29, 2005, now abandoned, which is a continuation of application No. 09/991,184, filed on Nov. 16, 2001, now Pat. No. 7,151,106, which is a continuation of application No. 09/463,097, filed as application No. PCT/EP98/04427 on Jul. 16, 1998, now Pat. No. 6,894,051.

(30) Foreign Application Priority Data

Jul. 18, 1997    (CH) ..................... 1764/97

(51) Int. Cl.
C07D 401/14 (2006.01)
A61K 31/506 (2006.01)

(52) U.S. Cl. .................. 544/295; 514/252.18
(58) Field of Classification Search ................. 544/295; 514/252.18
See application file for complete search history.

(56) References Cited

U.S. PATENT DOCUMENTS

| 3,887,551 | A | | 6/1975 | Crisp et al. |
| 3,905,959 | A | | 9/1975 | Nakanishi |
| 3,956,279 | A | * | 5/1976 | Binderup et al. ............ 540/336 |
| 4,061,853 | A | | 12/1977 | Urech |
| 4,351,832 | A | | 9/1982 | Rakhit et al. |
| 5,521,184 | A | | 5/1996 | Zimmermann |
| 5,985,893 | A | | 11/1999 | Yu et al. |
| 6,048,866 | A | | 4/2000 | Hutchings et al. |
| 6,894,051 | B1 | | 5/2005 | Zimmermann et al. |

FOREIGN PATENT DOCUMENTS

WO    WO 85/00604    2/1985

OTHER PUBLICATIONS

Carter et al., Chemotherapy of Cancer, second edition, John Wiley & Sons, N.Y., N.Y., 1981, pp. 362-365.*

Carroll et al., www.bloodjournal.org at Novartis Farma Bham, Oct. 2008, pp. 4947-4952.*
Hollis Showalter H.D. et al., "Small Molecule Inhibitors of the Platelet-Derived Growth Factor Receptor, the Fibroblast Growth Factor Receptor, and Src Family Tyrosine Kinases," Pharmacol. Ther., vol. 76, Nos. 1-3, pp. 55-71 (1997).
Davey, R.J. et al., "Polymorphism in Molecular Crystals: Stabilization of a Metastable Form by Conformation Mimicry," J. Am. Chem. Soc. 1997, vol. 119, pp. 1767-1772 (1997).
Myllärniemi Marjukka et al., "Selective Tyrosine Kinase Inhibitor for the Platelet-Derived Growth Factor Receptor In Vitro Inhibits Smooth Muscle Cell Proliferation After Reinjury of Arterial Intima In Vivo," Cardiovascular Drugs and Therapy, vol. 13, pp. 159-168 (1999).
Byrn, Stephen et al., "Pharmaceutical Solids: A Strategic Approach to Regulatory Considerations," Pharmaceutical Research, vol. 12, No. 7, pp. 945-954 (1995).
Radebough, Galen W., "Preformulation," Remington: The Science and Practice of Pharmacy, 20th Edition, Chapter 83, pp. 1447-1462 (2000).
Zimmermann, Jürg et al., "Potent and Selective Inhibitors of the Abi-Kinase: Phenylaminopyrimidine (PAP) Derivatives,"Bioorganic & Medicinal Chemistry Letters, vol. 7(2), pp. 187-192 (1997).
Bilder et al., "Inhibitors of the Platelet-Derived Growth Factor Receptor Tyrosine Kinase," Cardiovascular Drug Reviews, vol. 14, No. 4, pp. 380-399 (1996).
Buchdunger et al., "Selective inhibition of the platelet-derived growth facgtor signal transduction pathway by a protein-tyrosine kinase inhibitor of the 2-phenylaminopyrimidine class" Proc. Natl. Acad. Sci., USA, vol. 92, pp. 2258-2562 (1995).
Buchdunger et al., "Inhibition of the Abl Protein-Tyrosine Kinase in Vitro and in Vivo by a 2-Phenylaminopyrimidine Derivatives," Cancer Research, pp. 100-104, Jan. 1, 1996.
Raymond et al., "Multicentre phase II study of imatinib mesylate in patients with recurrent glioblastoma: An EORTC:NDDG/BTG Intergroup Study," Journal of Clinical Oncology, 2004 ASCO Annual Meeting Proceedings, vol. 22(14S), Abstract 1501 (2004).

(Continued)

*Primary Examiner*—Shailendra Kumar
(74) *Attorney, Agent, or Firm*—George R. Dohmann

(57) ABSTRACT

The invention relates to a new crystalline form of the methanesulfonic acid addition salt of 4-(4-methylpiperazin-1-ylmethyl)-N-[4-methyl-3-(4-pyridin-3-yl)pyrimidin-2-ylamino)phenyl]-benzamide of formula 1, which may be used for example for tumour therapy.

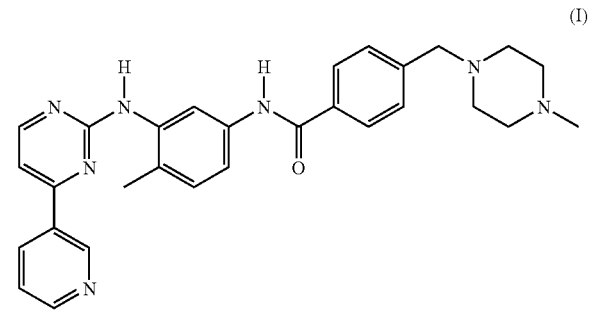

(I)

4 Claims, 2 Drawing Sheets

OTHER PUBLICATIONS

Wen et al., "Phase I study of STI571 (Gleevec) for patients with recurrent malignant gliomas and meningiomas (NABTRC 99-08)," Journal of Clinical Oncology, 2002 ASCO Annual Meeting, Abstract 288 (2002).

Wen et al., "Phase I/II Study of Imatinib Mesylate (STI571) for Patients with Recurrent Malignant Gliomas (NABTC 99-08)," Society of Neuro-Oncology 9th Annual Meeting 2004, Abstract TA63 (2004).

Kilic et al., "Intracranial Inhibition of Platelet-derived Growth Factor-mediated Glioblastoma Cell Growth by an Orally Active Kinase Inhibitor of the 2-Phenylaminopyrimidine Class," Cancer Research, 60, pp. 5143-5150 (2000).

Zografi et al., "Interfacial Phenomena," Remington Pharmaceutical Sciences, 18th Edition, Chapt. 19, pp. 257, 275, 276 (1990).

Jendrossek et al., "Novel Chemotherapeutic Agents for the Treatment of Glioblastoma Multiforme," Expert Opinions on Investigational Drugs, p. 1899-1924 (2003).

* cited by examiner

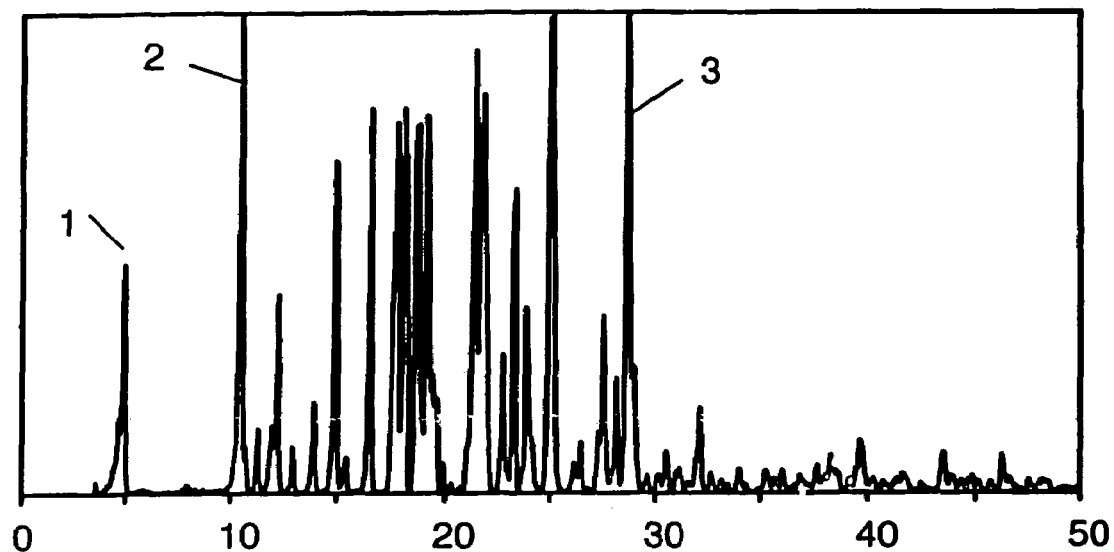
FIG 1 (alpha form)
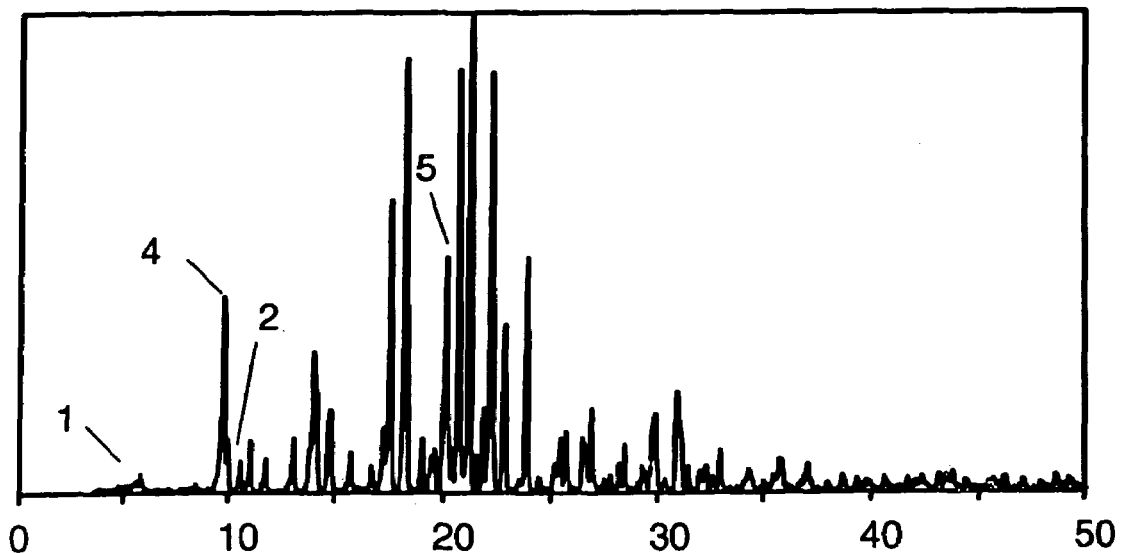
FIG 2 (beta form)

CRYSTAL MODIFICATION OF A N-PHENYL-2-PYRIMIDINEAMINE DERIVATIVE, PROCESSES FOR ITS MANUFACTURE AND ITS USE

This application is a continuation of U.S. application Ser. No. 11/241,266, filed Sep. 29, 2005, now abandoned, which is a continuation of U.S. application Ser. No. 09/991,184, filed Nov. 16, 2001, which is a continuation of U.S. application Ser. No. 09/463,097, filed Jan. 18, 2000, which is a 371 of PCT/EP98/04427, filed Jul. 16, 1998.

The invention relates to a particular form of the methanesulfonic acid addition salt of 4-(4-methylpiperazin-1-ylmethyl)-N-[4-methyl-3-(4-pyridin-3-yl)pyrimidin-2-ylamino) phenyl]-benzamide, comprising certain crystals, processes for the preparation thereof, pharmaceutical compositions containing this crystal form, and their use in diagnostic methods or preferably for the therapeutic treatment of warm-blooded animals, especially humans, or their use for the preparation of pharmaceutical preparations for use in diagnostic methods or preferably for the therapeutic treatment of warm-blooded animals, especially humans.

BACKGROUND OF THE INVENTION

The preparation of 4-(4-methylpiperazin-1-ylmethyl)-N-[4-methyl-3-(4-pyridin-3-yl)pyrimidin-2-ylamino)phenyl] benzamide and the use thereof, especially as an anti-tumour agent, are described in Example 21 of EP-A-0 564 409, which was published on 6 Oct. 1993, and in equivalent applications in numerous other countries. This compound is exemplified in these publications only in free form (not as a salt).

It has now been surprisingly found that a crystal form may under certain conditions be found in the methanesulfonate salt of this compound, which is described hereinafter as β-crystal form, and which has very advantageous properties.

DETAILED DESCRIPTION OF THE INVENTION

The invention is described in more detail in the following with the help of drawings and other aids:

DESCRIPTION OF THE DRAWINGS

FIG. 1/3 shows the X-ray diffraction diagram of the α-crystal form of the methanesulfonic acid addition salt of a compound of formula I.

FIG. 2/3 shows the X-ray diffraction diagram of the β-crystal form of the methanesulfonic acid addition salt of a compound of formula I.

Figure 3:
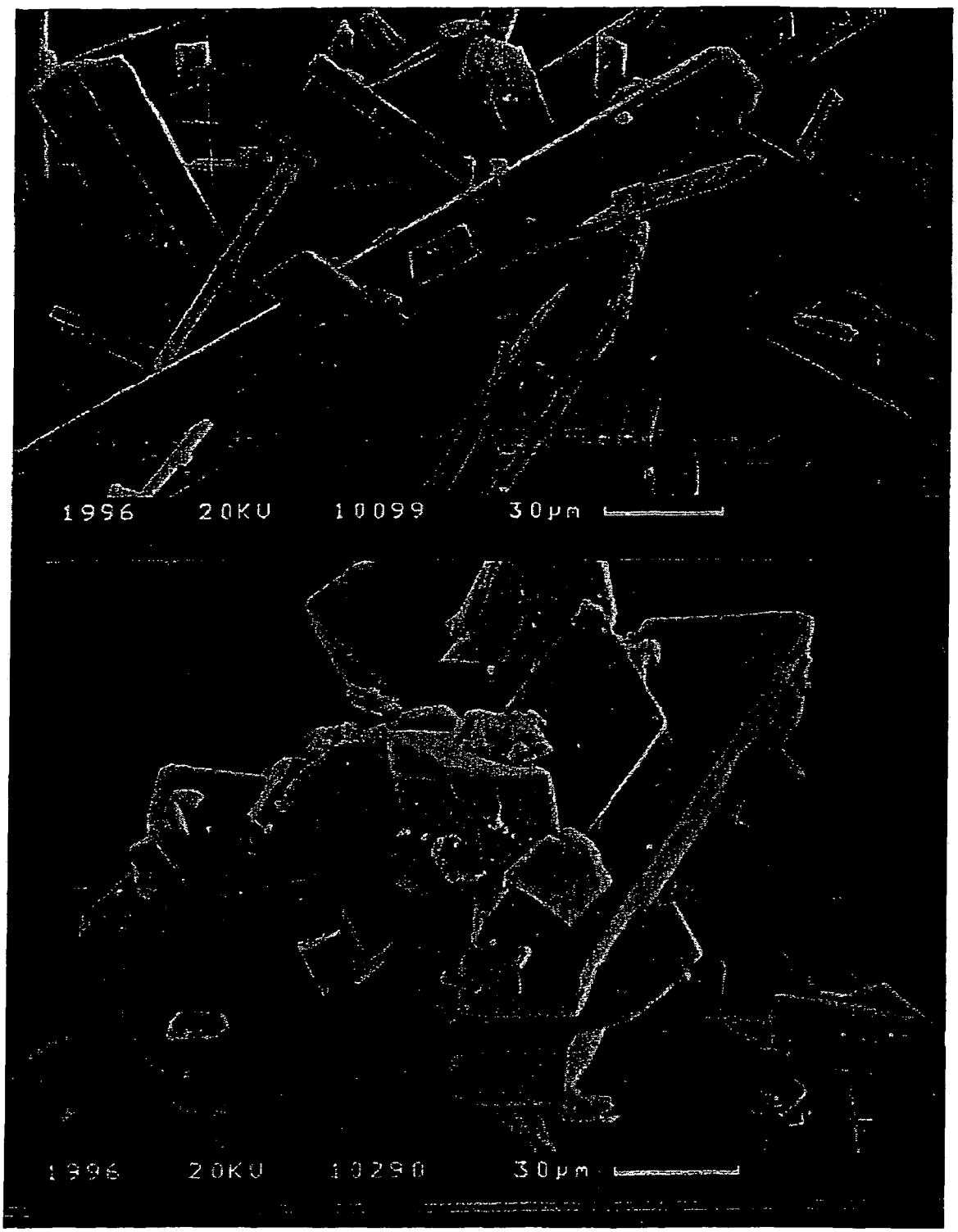
FIG. 3/3 shows the crystals above of the α-crystal form and below of the β-crystal form of 4-(4-methylpiperazin-1-ylmethyl)-N-[4-methyl-3-(4-pyridin-3-yl)pyrimidin-2-ylamino) phenyl]-benzamide methanesulfonate (=of the methanesulfonic acid addition salt of a compound of formula I).

In both X-ray diagrams, the angle of refraction 2theta is plotted on the horizontal axis (x-axis) and the relative line intensity (background-corrected peak intensity) on the vertical (y-axis). The diagrams are obtained as follows: first, the x-ray diffraction diagram is recorded on film using a Guinier camera (Enraf-Nonius FR 552 model) with a Guinier 258-94c film and copper radiation (Kα1 radiation, wavelength λ=1.54060 Ångström). The optical density of the lines on the film is proportional to the light intensity. The film is then scanned in using a line scanner (LS 18, Johansson, Täby, Sweden) with SCANPI software.

In accordance with FIG. 2/3 there are lines having a relative line intensity of 20 or more at the following angles of refraction 2theta (relative line intensities given in parentheses): 9.70° (40), 13.9° (26),14.7° (23), 17.5° (57),18.2° (90), 20.0° (65), 20.6° (76), 21.1° (100), 22.1° (89), 22.7° (38), 23.8° (44), 29.8° (23) and 30.8° (20). The fact that in FIG. 2/3 the relative line intensity of the line at 30.8° seems to be higher than that of the line at 29.8° is due to a close by further line at 31.0° having a relative line intensity of 13.

Melting points are determined by means of a DSC thermogram using a Mettler-Toledo TA8000. DSC ("differential scanning calorimetry") is the technique of dynamic differential calorimetry. Using this technique, the melting temperature both of the α-crystal form and of the β-crystal form can be measured by heating the samples until a thermal, i.e. an endothermic or exothermic, reaction is detected by means of ultrasensitive sensors. The melting points indicated in this text are determined using a Mettler-Toledo TA8000 apparatus, about 5.5 to 6.5 mg of each sample being measured in an aluminium crucible with a perforated lid under a quiescent atmosphere of air at a heating rate of 10° C./min (starting at 20° C.).

The α-crystal form of 4-(4-methylpiperazin-1-ylmethyl)-N-[4-methyl-3-(4-pyridin-3-yl)pyrimi-din-2-ylamino)phenyl]benzamide methanesulfonate is characterised by needle-shaped crystals and is hygroscopic. In this form, the crystals are not particularly well-suited to pharmaceutical formulation as solid dosage forms, because their physical properties, for example their flow characteristics, are unfavourable. Under certain conditions, however, it is possible to obtain 4-(4-methylpiperazin-1-ylmethyl)-N-[4-methyl-3-(4-pyridin-3-yl)pyrimidin-2-ylamino)phenyl]benzamide methanesulfonate in a crystal form which is not needle-shaped. This form is described in the present text as β-crystal form.

The β-crystal form of 4-(4-methylpiperazin-1-ylmethyl)-N-[4-methyl-3-(4-pyridin-3-yl)pyrimidin-2-ylamino)phenyl]benzamide methanesulfonate has the advantage that its flow properties are substantially more favourable than those of the α-crystal form. This crystal form has the further advantage of being thermodynamically more stable at temperatures below 140° C. Finally, the β-crystal form is less hygroscopic than the α-crystal form and thus also stores better and is easier to process.

The invention relates to an acid addition salt of a compound of formula I comprising non-needle-shaped crystals, especially the β-crystal form of the methanesulfonic acid addition salt of the compound of formula I.

The invention relates especially to a particular, essentially pure crystal form, preferably that which is referred to hereinafter as the β-crystal form, of the methanesulfonic acid addition salt of 4-(4-methylpiperazin-1-ylmethyl)-N-[4-methyl-3-(4-pyrid-3-yl)pyrimidin-2-ylamino)phenyl]benzamide methanesulfonate of formula I,

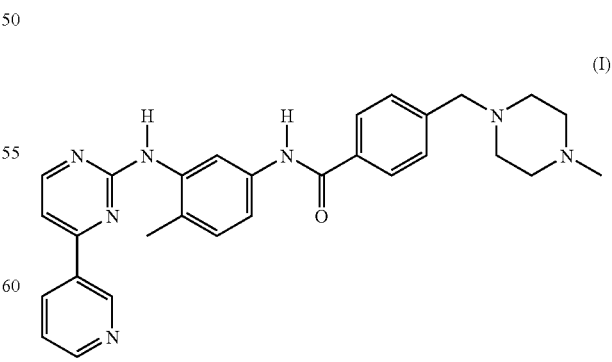

(I)

Where the term methanesulfonic acid salt of a compound of formula I or of 4-(4-methyl-piperazin-1-ylmethyl)-N-[4-methyl-3-(4-pyridin-3-yl)pyrimidin-2-ylamino)phenyl]ben zamide is used hereinbefore and hereinafter, this is especially taken to mean the methanesulfonic acid salt of formula II.

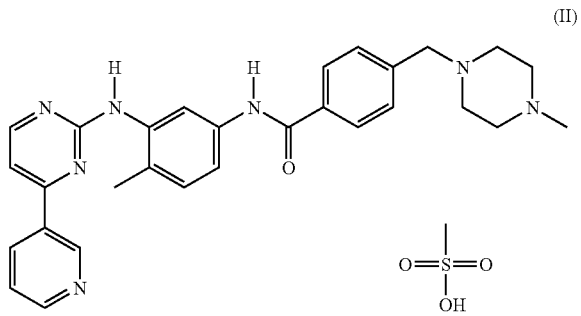

(II)

The term "essentially pure" is understood in the context of the present invention to mean especially that at least 90, preferably at least 95, and most preferably at least 99 per cent by weight of the crystals of an acid addition salt of formula I are present in the crystal form according to the invention, especially the β-crystal form, In the context with stating that the acid addition salt of formula II exhibits an X-ray diffraction diagram essentially as in FIG. 2/3 the term "essentially" means that at least the major lines of the diagram depicted in FIG. 2/3, i.e. those having a relative line intensity of more than 10%, especially more than 20%, as compared to the most intense line in the diagram, have to be present.

The invention expressly relates also to those forms of the methanesulfonic acid addition salt of a compound of formula I in which crystals of the crystal form according to the invention, especially the β-crystal form, are present in essentially pure form along with other crystal forms and/or the amorphous form of the 4-(4-methyl-piperazin-1-ylmethyl)-N-[4-methyl-3-(4-pyridin-3-yl)pyrimidin-2-ylamino)phenyl]benzamide methanesulfonate. Preferred, however, is the acid addition salt of formula II, which is present in essentially pure form in the β-crystal form.

The new crystal form, especially the β-crystal form, has the following properties:

The melting point in the DSC thermogram of the β-crystal form is 217° C., and that of the α-crystal form is 226° C. (start of melting).

The X-ray diffraction diagram of the β-crystal form does not show the peak of the α-crystal form marked (1) and only to a very minor extent shows that marked (3) (see FIGS. 1/3 and 2/3). By contrast FIG. 2/3 shows a new additional peak marked (4). The new peak marked (5) also appears in FIG. 2/3.

The X-ray diffraction diagrams also show other marked differences.

In the preferred embodiment, the essentially pure methanesulfonic acid addition salt of a compound of formula I in the β-crystal form shows the X-ray diffraction diagram indicated in FIG. 2/3.

(i) Preferred is a crystal form of the methanesulfonic acid addition salt of a compound of formula I which does not show the peak marked (1) in FIG. 1/3 on the X-ray diffraction diagram, this crystal form preferably being present in essentially pure form.

(ii) Preferred is also a crystal form of the methanesulfonic acid addition salt of a compound of formula I which remains dry at 93% relative humidity and at a temperature of 25° C., this crystal form preferably being present in essentially pure form.

(iii) The invention relates preferably to the β-crystal form of the methanesulfonic acid addition salt of a compound of formula I which is characterised by the presence of crystals displaying the form shown in FIG. 3/3 below; especially the β-crystal form in essentially pure form.

(iv) Stronger preference is for the β-crystal form of the methanesulfonic acid addition salt of a compound of formula I which has a melting point of less than 225° C., especially between 217 and 225° C.

(v) Stronger preference is also for the β-crystal form of the methanesulfonic acid addition salt of a compound of formula I which has a melting point of less than 217° C., defined as the start of melting in the DSC thermogram.

(v) Stronger preference is also for the β-crystal form of the methanesulfonic acid addition salt of a compound of formula I which on X-ray diffraction shows the peak marked (4) in FIG. 2/3.

(vii) Stronger preference is also for the β-crystal form of the methanesulfonic acid addition salt of a compound of formula I which on X-ray diffraction shows the peak marked (5) in FIG. 2/3.

(viii) Still stronger preference is for the β-crystal form of the methanesulfonic acid addition salt of a compound of formula I which shows an X-ray diffraction diagram of the type shown in FIG. 2/3, especially one in which the relative peak intensities of each peak do not deviate by more than 10% from the relative peak intensities in the diagram shown in FIG. 2/3, especially an X-ray diffraction diagram identical to that shown in FIG. 2/3.

(ix) Greatest preference is for the β-crystal form of the methanesulfonic acid addition salt of a compound of formula I which has two of the properties named in paragraphs (i) to (viii), greater preference being for three of the properties in the said paragraphs, especially all the said properties, and most especially those properties defined as being preferred.

Likewise strongly preferred is a crystal form as defined in one of the paragraphs (i) to (ix) in essentially pure form.

Particularly special preference is for the β-crystal form of the methanesulfonic acid addition salt of a compound of formula I obtainable as described in the Examples.

In all cases, a form of the methanesulfonic acid addition salt of a compound of formula I comprising the corresponding above-mentioned crystal form is also taken to be meant in a wider aspect of the invention.

The (preferably essentially pure) β-crystal form is obtainable by a) digesting another crystal form, especially the α-crystal form, or an amorphous starting material of the methanesulfonic acid addition salt of a compound of formula I, with a suitable polar solvent, especially an alcohol, most especially methanol, or also a ketone (especially in a mixture with water, for example water/acetone), typically acetone, a N,N-di-lower alkyl-lower alkanecarboxamide, typically N,N-dimethylformamide or -acetamide, or a hydrophilic ether, typically dioxane, preferably in the presence of some water, or mixtures thereof, in suspension at a suitable temperature, preferably a temperature between 20 and 50° C., for example at about 25° C., or b) dissolving another crystal form, especially the α-crystal form, or an amorphous starting material of the methanesulfonic acid addition salt of a compound of formula I, with a suitable polar solvent, such as especially an alcohol, typically methanol or ethanol, a ketone (especially in a mixture with water, for example water/acetone) typically acetone, a N,N- di-lower alkyl-lower alkanecarboxamide, typically N,N-dimethylformamide or -acetamide, or a hydrophilic ether, typically dioxane, or mixtures thereof, preferably in the presence of some water, at a suitable temperature, especially after heating the solvent, or while warming during the dissolution process, in both cases preferably to 25° C. up to the reflux temperature of the reaction mixture, and then initiating crystallisation by adding a small amount of the β-crystal form as seed crystal at a suitable temperature, for example between 0 and 70° C., preferably between 20 and 70° C.

The educt, the α-crystal form of the methanesulfonic acid addition salt of 4-(4-methyl-piperazin-1-ylmethyl)-N-[4-methyl-3-(4-pyridin-3-yl)pyrimidin-2-ylamino)phenyl]benzamide, is obtainable for example by precipitating out the salt from a solution in a solvent other than an alcohol, such as methanol, and without adding a seed crystal of the β-crystal form.

The above conditions on the selective preparation of the individual crystal forms are not conclusive. In general, for example, it is possible to vary parameters such as the weight ratio of the methanesulfonic acid addition salt of a compound of formula I to the solvent. It is also possible to vary the time needed for the preparation of the β-crystal form, especially when the temperatures are adjusted at the same time.

One of the advantages of the β-crystal form is especially its more compact crystal form, which results substantially more beneficial flow properties and thus in better processability of the methanesulfonic acid addition salt of a compound of formula I in the β-crystal form versus the α-crystal form, for example in the manufacture of pharmaceutical preparations.

It is true to say that the α-crystal form of the methanesulfonic acid addition salt of a compound of formula I is metastable at room temperature. However, the β-crystal form of the methanesulfonic acid addition salt of a compound of formula I is the thermodynamically stable form at room temperature. Greater stability is thus to be expected.

Finally, the β-crystal form is less hygroscopic than the α-crystal form of the methanesulfonic acid addition salt of a compound of formula I, as can be shown by the following table:

On measurement of the crystal forms up to the point where equilibrium is reached (no further adsorption) in a glass climatic chamber at 25° C. and at the humidities shown below, the following water content values are found (the % values for the final water content refer to dry weight):

| Relative humidity | Final water content on adsorption | | | |
|---|---|---|---|---|
| | α-crystal form | | β-crystal form | |
| (%) | (%) | (molar) | (%) | (molar) |
| 12 | 0.14 | 0.05 | 0.08 | 0.02 |
| 33 | 0.18 | 0.06 | 0.10 | 0.03 |
| 46 | 0.14 | 0.05 | — | — |
| 54 | 0.13 | 0.04 | 0.14 | 0.05 |
| 66 | 0.07 | 0.02 | 0.09 | 0.03 |
| 75 | 0.49 | 0.16 | — | — |
| 85 | 0.18 | 0.06 | 0.16 | 0.05 |
| 93 | 40 | 13.1 | 0.15 | 0.05 |
| 97 | 63 | 20.8 | 23 | 7.5 |
| 100 | — | — | 37 | 12 |

It is shown that, at 25° C., the α-crystal form is hygroscopic and rapidly takes up water so that, at 93% relative humidity, the sample is to some extent present in amorphous form, whereas the β-crystal form remains dry under these conditions. Both crystal forms liquify at 97% relative humidity, but this happens very much more quickly with the α-crystal form than with the β-crystal form.

The lower hygroscopicity is a further advantage for processing and storing the acid addition salt in the β-crystal form.

The methanesulfonic acid addition salt of a compound of formula I, which is preferably used in the β-crystal form (hereinafter, the methanesulfonic acid addition salt is always taken to mean the β-crystal form), as well as 4-(4-methylpiperazin-1-ylmethyl)-N-[4-methyl-3-(4-pyridin-3-yl)pyrimidin-2-ylamino)phenyl]benzamide in free form, possesses valuable pharmacological properties and may, for example, be used as an anti-tumour agent, as an agent to treat atherosclerosis, as an agent to treat restenosis, for the prevention of transplantation-induced disorders, such as obliterative bronchiolitis, and/or for preventing the invasion of warm-blooded animal cells by certain bacteria, such as *Porphyromonas gingivalis*.

The phosphorylation of proteins has long been known as an essential step in the differentiation and division of cells. Phosphorylation is catalysed by protein kinases subdivided into serine/threonine and tyrosine kinases. The tyrosine kinases include PDGF (Platelet-derived Growth Factor) receptor tyrosine kinase.

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis.

The inhibition of PDGF-stimulated receptor tyrosine kinase activity in vitro is measured in PDGF receptor immune complexes of BALB/c 3T3 cells, as described by E. Andrejauskas-Buchdunger and U. Regenass in Cancer Research 52, 5353-5358 (1992). A compound of formula I described in more detail hereinbefore, such as especially its β-crystal form, inhibits PDGF-dependent acellular receptor phosphorylation. The inhibition of PDGF receptor tyrosine kinase is measured in a microtitre ELISA assay (cf Trinks et al., J. Med. Chem. 37, 1015-27 (1994). 4-(4-Methylpiperazin-1-ylmethyl)-N-[4-methyl-3-(4-pyridin-3-yl)pyrimidin-2-ylamino)phenyl]benzamide and the corresponding methanesulfonate salt inhibit the tyrosine kinase activity of the PDGF receptor at an $IC_{50}$ (concentration at which activity is inhibited by 50% compared with the control) of about 120 nM and about 100 nM, respectively.

The inhibition of PDGF makes a compound of formula I also suitable for the treatment of tumour diseases, such as gliomas, sarcomas, prostate tumours, and tumours of the colon, breast, and ovary.

The methanesulfonic acid addition salt of a compound of formula I also inhibits cellular processes involving the so-called stem-cell factor (SCF, also known as the c-kit ligand or steel factor), such as SCF receptor (kit) autophosphorylation and the SCF-stimulated activation of MAPK kinase (mitogen-activated protein kinase).

The methanesulfonic acid addition salt of a compound of formula I, such as especially the β-crystal form thereof, thus inhibits also the autophosphorylation of SCF receptor (and c-kit, a proto-oncogen). MO7e cells are a human promegakaryocytic leukaemia cell line which depends on SCF for proliferation. They are obtained from Grover Bagby, Oregon Health Sciences University, USA. The cells are cultivated in RPMI 1649 medium supplemented with 10 FBS and 2.5 ng/ml GC-CMF. GM-SCF and SCF are commercially available. Serum-deprived MO7e cells are prepared and incubated for 90 min at 37° C. with the test substance before being stimulated with recombinant SCF for 10 min at 37° C. Identical quantities of cell lysates are analysed by Western blot using antiphosphotyrosine antibodies (Buchdunger et al., Proc. Natl. Acad. Sci (USA) 92, 2558-62 (1995)). The immunodecorated proteins are detected by means of the ECL Western blotting system from Amersham (Amersham, UK). A compound of formula I, especially the crystal form of the methanesulfonate salt of formula II, inhibits the autophosphorylation of SCF-R in the micromolar range.

On the basis of the described properties, the methanesulfonic acid addition salt of a compound of formula I, such as especially the β-crystal form thereof, may be used not only as a tumour-inhibiting substance, for example in small cell lung cancer, but also as an agent to treat non-malignant proliferative disorders, such as atherosclerosis, thrombosis, psoriasis, scleroderma, and fibrosis, as well as for the protection of stem cells, for example to combat the haemotoxic effect of chemotherapeutic agents, such as 5-fluoruracil, and in asthma. It may especially be used for the treatment of diseases which respond to an inhibition of the PDGF receptor kinase.

In addition, the methanesulfonic acid addition salt of a compound of formula I, such as especially its β-crystal form C, prevents the development of multidrug resistance in cancer therapy with other chemotherapeutic agents or abolishes a pre-existing resistance to other chemotherapeutic agents. Also regardless of the effect described hereinbefore, the methanesulfonic acid addition salt of a compound of formula I, such as especially the β-crystal form thereof, may be used to advantage in combination with other antitumor agents.

Also abl kinase, especially v-abl kinase, is inhibited by 4-(4-methylpiperazin-1-ylmethyl)-N-[4-methyl-3-(4-pyridin-3-yl)pyrimidin-2-ylamino)phenyl]benzamide and its methanesulfonate salt. The inhibition of v-abl tyrosine kinase is determined by the methods of N. Lydon et al., Oncogene Research 5, 161-173 (1990) and J. F. Geissler et al., Cancer Research 52, 4492-8 (1992). In those methods [Val$^5$]-angiotensin II and [γ$^{-32}$P]-ATP are used as substrates. 4-(4-Methylpiperazin-1-ylmethyl)-N-[4-methyl-3-(4-pyridin-3-yl)-pyrimidin-2-ylamino)phenyl]benzamide here shows an IC$_{50}$ of 38 nM.

By analogy, the salt of a compound of formula I also inhibits BCR-abl kinase (see Nature Medicine 2, 561-566 (1996)) and is thus suitable for the treatment of BCR-abl-positive cancer and tumour diseases, such as leukaemias (especially chronic myeloid leukaemia and acute lymphoblastic leukaemia, where especially apoptotic mechanisms of action are found), and also shows effects on the subgroup of leukaemic stem cells as well as potential for the purification of these cells in vitro after removal of said cells (for example, bone marrow removal) and reimplantation of the cells once they have been cleared of cancer cells (for example, reimplantation of purified bone marrow cells).

In addition, the methanesulfonic acid addition salt of a compound of formula I shows useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids. If 4-(4-methylpiperazin-1-ylmethyl)-N-[4-methyl-3-(4-pyridin-3-yl)pyrimidin-2-ylamino)phenyl]benzamide methanesulfonate, especially in the β-crystal form, is administered to rats with tracheal allogenic transplants, for example in a dose of 50 mg/kg i.p., it can be shown after removal of 10 transplants per group after 10 and 30 days for morphometric analysis of possible epithelial lesions and occlusion of the airways, and investigation for immunohistochemical pathways of action that, although the methanesulfonic acid addition salt of a compound of formula I has no significant effect on epithelial necrosis or infiltration by inflammatory cells, it does markedly reduce fibroproliferation and occlusion of the lumen compared with controls. Synergistic effects with other immunomodulatory or anti-inflammatory substances are possible, for example when used in combination with ciclosporin, rapamycin, or ascomycin, or immunosuppressant analogues thereof, for example ciclosporin A (CsA), ciclosporin G, FK-506, rapamycin, or comparable compounds; corticosteroids; cyclophosphamide; azathioprine; methotrexate; brequinar; leflunomide; mizoribine; mycophenolic acid; mycophenolate mofetil; 15-deoxyspergualin; immunsuppressant antibodies, especially monoclonal antibodies for leucocyte receptors, for example MHC, CD2, CD3, CD4, CD7, CD25, CD28, B7, CD45, CD58 or their ligands; or other immunomodulatory compounds, such as CTLA4lg. If CsA (1 mg/kg s.c.), for example, is combined with the acid addition salt of formula I (50 mg/kg), synergism may be observed.

The methanesulfonic acid addition salt of a compound of formula I is also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the methanesulfonic acid addition salt of a compound of formula I and also by investigating its effect on the thickening of the vascular intima following mechanical injury in vivo.

The methanesulfonic acid addition salt of a compound of formula I is used in 0.1N HCl or DMSO at a concentration of 10 mM for in vitro studies. The stock solution is further diluted with cell culture medium and used in concentrations of 10 to 0.1 μM for the experiments. For in vivo administration, the methanesulfonic acid addition salt of a compound of formula I is dissolved for example in DMSO at a concentration of 200 mg/ml and then diluted 1:20 with 1% Tween in 0.9% saline solution. After sonication, a clear solution is obtained. The stock solutions are prepared fresh each day before administration. (The compound of formula I may also be dissolved simply in deionised water for oral administration or in 0.9% saline solution for parenteral administration). Administration is carried out 24 hours before the operation. The methanesulfonic acid addition salt of a compound of formula I is administered to rats in one dose of 50 mg/kg i.p. per day for the entire observation period. Control rats are given the same dose of substrate. Oral administration is also possible.

Primary cultures of smooth-muscle aorta cells are isolated from 9 to 11 -day-old DA (AG-B4, RT1 a) rat aorta using a modification of the method described by Thyberg et al. (see Differentiation 25, 156-67 (1983)). The aorta is opened by means of a longitudinal incision and the endothelium carefully removed. The adventitia and the tunica media are separated, and the tunica media is digested with 0.1% collagenase and DNAse in phosphate-buffered physiological saline for 30 min at 37° C. The cells are centrifuged, suspended in culture medium, and then allowed to grow on plastic vials. The primary cells are used for the experiments after passages 2 to 6. Subcultures are kept in DMEM (Dulbecco's Modified Eagle's Medium), supplemented with 10% fetal calf serum, 2 mmol/ml glutamine, 100 mmol/ml streptomycin, and 100 IU/mi penicillin. For identification purposes, the cells are left to grow on glass slide covers and stained on SMC-α actin (see below).

The migration of smooth-muscle cells is quantified in vitro using a Transwell cell culture insert (Costar, Cambridge, Mass.) whose upper and lower compartments are separated by a polycarbonate membrane of 8 μm pore size. The cells (100 μl at a concentration of 1 million cells/ml) are exposed in the upper compartment. After 2 hours, 60 ng/ml PDGF-BB or PDGF-AA (Upstate Biotechnology Inc., Lake Placid, N.Y.) is added to the lower compartment, supplemented with 0.5% fetal calf serum and 0.1% bovine serum albumin, and the test compound is added in concentrations of 3, 1, 0.3, 0.1, 0.03, 0.01, and 0.003 μM. To measure fibronectin-dependent migration, the Transwell chambers are covered with fibronectin at a concentration of 10 μg/ml for 24 h at 4° C. (human cellular fibronectin, Upstate Biotechnology Inc.). After 24 hours' migration, the filters are removed, fixed in methanol, and stained with Mayer's haematoxylin and eosin. The migrated cells on the lower side of the filter membrane are determined by counting the specified sectional fields on the filters with the aid of a light microscope with a magnification of 400×. The inhibition of migration is quantified in terms of the percentage of cells versus with the control. To exclude the possibility of a toxic effect, the viability of the cells is tested by incorporation of 3H-thymidine in DMEM, supplemented with 10% fetal calf serum. An inhibition of migration induced by PDGF-M and especially by PDGF-BB is observed.

Experimental animals: the aorta and carotid artery of male Wistar rats (purchased from the Laboratory Animal Center of the University of Helsinki, Finland) are denuded. The rats are anaesthetised with 240 mg/kg chloral hydrate i.p. Buprenorphine (Temgesic, Reckitt & Coleman, Hull, UK) is administered for perioperative and postoperative alleviation of pain. All animals are given human care in keeping with the "Principles of Laboratory Animal Care" and the "Guide for the Care and Use of Laboratory Animals" of the NIH (NIH Publication 86-23, revised 1985). Rats weighing 200-300 g were used for the denudation procedure. The left common carotid artery is denuded of endothelium through the intraluminal passage of a 2F embolectomy catheter (Baxter Healthcare Corporation, Santa Ana, Calif., 27). To remove the endothelium, the catheter is passed through the lumen three times, inflated with 0.2 ml air. The external carotid is ligated after removal of the catheter and the wound closed. The histological changes are evaluated by reference to sections of mid-carotid 4 days after denudation. The thoracic aorta is denuded of endothelium using a 2F Fogarty arterial embolectomy catheter. The catheter is inserted into the thoracic aorta via the left iliac artery, inflated with 0.2 ml air, and passed through the lumen five times to remove the endothelium. The iliac artery is then ligated. Three times (3, 7 and 14 days) are selected for evaluation of the histological changes.

To quantify the proliferating cells, 3 different procedures are used for labelling the cells with bromodeoxyuridine (BrdU) after denudation of the rat carotid. In this model, the media cell proliferation begins 24 h after denudation; cells in the intima first appear after 72-96 hours. To quantify the proliferation of smooth-muscle cells before the appearance of cells in the intima, 0.1 ml BrdU-labelling reagent (ZYMED, San Francisco, Calif.) is administered i.v. during the postoperative period of 0 to 72 h post-denudation (in total 0.1 ml 6 times). To quantify the proliferation during the initial wave of migration, the rats were given 3×0.1 ml BrdU-labelling reagent at 8-hour intervals over a period of 72-96 hours after the operation. To quantify the proliferation at the end of the initial wave of migration, a third group of rats is given a pulsed dose of 0.3 ml BrdU three hours before sacrifice.

Histological samples are fixed in 3% paraformaldehyde solution for 4 h for embedding in paraffin. Morphological changes are evaluated from paraffin sections stained with Mayer's haematoxylin-eosin. The cell counts of different vessel sections are calculated at a magnification of 400×. To identify cells in culture and cells appearing in the neo-intima within four days of the denudation injury, immunohistochemical staining of acetone-fixed samples is carried out using an anti-a-actin antibody obtained from smooth-muscle cells (Bio-Makor, Rehovot, Israel). Primary smooth-muscle cells are identified on acetone-fixed glass cover slides using the same staining method. The sections are incubated with the primary antibody (dilution 1:2000), washed, and incubated consecutively with peroxidase-conjugated rabbit-antimouse-Ig and goat-antirabbit-Ig, followed by treatment with substrate solution with the chromogen 3-amino-9-ethylcarbazol and hydrogen peroxide. BrdU stains are prepared from paraffin sections using a primary mouse antibody (Bu20a, Dako, A/S, Denmark) and the Vectastain Elite ABC-Kit (Vector Laboratories, Burliname, Calif.). The sections are deparaffinised and treated by microwave at 500 W (2×5 min in 0.1M citrate buffer, pH 6), followed by treatment with 95% formamide in 0.15M trisodium citrate for 45 min at 70° C. Antibody dilutions are prepared according to the manufacturer's specifications. The sections are counterstained with Mayer's haematoxylin and eosin, and positive cells are counted separately for the initima, media, and adventitia.

In the carotid of treated animals, a significant decrease is found in the cell count for smooth-muscle cells. The adventitia and the media showed a significant reduction in the cell count. As a result of the methanesulfonic acid addition salt of a compound of formula I, a slight decrease in the absolute number of BrdU-labelled cells is seen in the intima, media, and adventitia during the first two labelling periods (0-72 and 72-96 h), and after 93-96 h a decrease in the number of labelled cells is seen in all compartments. Decreases in the number of smooth-muscle cells are likewise found in the aorta-denuded animals.

According to these findings, the methanesulfonic acid addition salt of a compound of formula I can thus inhibit the proliferation, and especially the migration, of vascular smooth-muscle cells.

The methanesulfonic acid addition salt of a compound of formula I, especially the β-crystal form, is also capable of inhibiting angiogenesis. This may be demonstrated as follows: a chamber containing agar (0.8%) and heparin (2 U/ml) with or without growth factor (VEGF 3 μg/ml, PDGF 1 μg/ml or bFGF 0.3 μg/ml) is implanted subcutaneously into normal mice (C57 BL/6). The methanesulfonic acid addition salt of a compound of formula I is administered orally in a dose showing good anti-tumour activity in a nude mouse xenotransplant model. Dosing is started one day before implantation of the chambers. The chambers are removed after 5 days. The angiogenic efficacy is quantified by measuring both the vascularised tissue which has grown around the implant and the blood content of this tissue (external blood). The blood is determined by measuring the haemoglobin. Although the vessels do not grow into the agar, the agar becomes intensely red if an antiangiogenic effect is present. If a compound inhibits the increase in blood that is induced by the growth factor, this is seen as an indication that the compound in question is blocking the angiogenic effect of the growth factor concerned. Inhibition of the weight but not the volume of blood suggests an effect on the proliferation of fibroblasts. A suppression of the control response suggests an inhibition of wound healing. At an oral dose of 50 mg/kg once daily, the compound of formula I inhibits the angiogenic effect of all three growth factors (VEGF, PDFG, bFGF).

It goes without saying that all the indicated inhibitory and pharmacological effects are also found with the free base, 4-(4-methylpiperazin-1-ylmethyl)-N-[4-methyl-3-(4-pyridin-3-yl)pyrimidin-2-ylamino)phenyl]benzamide, or other salts thereof. The present invention relates especially to the β-crystal form of the methanesulfonic acid addition salt of a compound of formula I in the treatment of one of the said diseases or in the preparation of a pharmacological agent for the treatment thereof.

The antiproliferative, especially anti-tumour, activity of the methanesulfonic acid addition salt of a compound of formula I in vivo is, for example, described for the treatment of abl-dependent tumours in Nature Med. 2, 561-6 (1996).

The invention relates also to a process for the treatment of warm-blooded animals suffering from said diseases, especially a tumour disease, wherein a quantity of the β-crystal form of the methanesulfonic acid addition salt of a compound of formula I which is effective against the disease concerned, especially a quantity with antiproliferative and especially tumour-inhibiting efficacy, is administered to warm-blooded animals in need of such treatment. The invention relates moreover to the use of the β-crystal form of the methanesulfonic acid addition salt of a compound of formula I for the inhibition of the above-mentioned tyrosine kinases, especially PDGF receptor kinase, v-abl kinase, and/or c-kit receptor kinase, or for the preparation of pharmaceutical compositions for use in treating the human or animal body, especially for the treatment of tumours, such as gliomas, ovarian tumours, prostate tumours, colon tumours, and tumours of the lung, such as especially small cell lung carcinoma, and tumours of the breast or other gynaecological tumours. Depending on species, age, individual condition, mode of administration, and the clinical picture in question, effective doses, for example daily doses of about 1-2500 mg, preferably 1-1000 mg, especially 5-500 mg, are administered to warm-blooded animals of about 70 kg bodyweight.

The invention relates also to pharmaceutical preparations which contain an effective amount, especially an effective amount for prevention or treatment of one of the said diseases, of the methanesulfonic acid addition salt of a compound of formula I in the β-crystal form, together with pharmaceutically acceptable carriers which are suitable for topical, enteral, for example oral or rectal, or parenteral administration and may be inorganic or organic and solid or liquid. Especially tablets or gelatin capsules containing the active substance together with diluents, for example lactose, dextrose, sucrose, mannitol, sorbitol, cellulose, and/or glycerin, and/or lubricants, for example silica, talc, stearic acid, or salts thereof, typically magnesium or calcium stearate, and/or polyethylene glycol, are used for oral administration, Tablets may likewise contain binders, for example magnesium aluminium silicate, starches, typically corn, wheat or rice starch, gelatin, methylcellulose, sodium carboxymethylcellulose and/or polyvinylpyrrolidone, and, if so desired, disintegrants, for example starches, agar, alginic acid, or a salt thereof, typically sodium alginate, and/or effervescent mixtures, or adsorbents, colouring agents, flavours, and sweetening agents. The pharmacologically active compounds of the present invention may further be used in the form of preparations for parenteral administration or infusion solutions. Such solutions are preferably isotonic aqueous solutions or suspensions, these possibly being prepared before use, for example in the case of lyophilised preparations containing the active substance either alone or together with a carrier, for example mannitol. The pharmaceutical substances may be sterilised and/or may contain excipients, for example preservatives, stabilisers, wetting agents and/or emulsifiers, solubilisers, salts for the regulation of osmotic pressure, and/or buffers. The present pharmaceutical preparations which, if so desired, may contain further pharmacologically active substances, such as antibiotics, are prepared in a manner known per se, for example by means of conventional mixing, granulating, coating, dissolving or lyophilising processes, and contain from about 1% to 100%, especially from about 1% to about 20%, of the active substance or substances.

The following Examples illustrate the invention without limiting the scope thereof. $R_f$-values are determined on TLC plates coated with silica gel (Merck, Darmstadt, Germany). The ratio of the solvents to one another in the solvent systems used is indicated by volume (v/v), and temperatures are given in degrees celsius (° C.).

Eluents (Gradients):

HPLC gradient:

0% b) in a) for 20 minutes, then 0%→30% b) in a) for 10 minutes, then 30% b) in a) for 5 minutes.

Eluent a): Ion pairing reagent and methanol (420 ml+580 ml)

Eluent b): Ion pairing reagent and methanol (40 ml+960 ml)

Ion pairing reagent: 7.5 g 1-octanesulfonic acid dissolved in about 800 ml water, pH value adjusted to 2.5 with phosphoric acid, and diluted with water to 1000 ml.

Column: 150×3.9 mm, packed with Symmetry C18 5μ (Waters), pre-equilibrated with eluent a).

Flow rate 1.2 ml/min, UV detection at 267 nm.

EXAMPLES

Example 1

Preparation of β-Crystal form of 4-(4-methylpiperazin-1-ylmethyl)-N-[4-methyl-3-(4-pyridin-3-yl) pyrimidin-2-ylamino)phenyl]benzamide methanesulfonate—Variant 1

An 11% (w/w) suspension of 4-(4-methylpiperazin-1-ylmethyl)-N-[4-methyl-3-(4-pyridin-3-yl)-pyrimidin-2-ylamino)phenyl]benzamide methanesulfonate in the α-crystal form is digested in methanol for two days at about 25° C. The crystals are isolated by filtration on a glass filter with a G4 frit and dried overnight at room temperature on filter paper. Smp (by DSC): 217° C. (start of melting).

The starting material, 4-(4-methylpiperazin-1-ylmethyl)-N-[4-methyl-3-(4-pyridin-3-yl)pyrimid-in-2-ylamino)phenyl]benzamide methanesulfonate is prepared as follows: 98.6 g (0.2 mol) free 4-(4-methylpiperazin-1-ylmethyl)-N-[4-methyl-3-(4-pyridin-3-yl)pyrimidin-2-ylamino)phenyl]benzamide (for preparation see, for example, EP-A-0 564 409) is added to 1.4 l ethanol. To this beige suspension, 19.2 g (0.2 mol) methanesulfonic acid is added dropwise over a period of 20 minutes. The solution is heated under reflux for 20 minutes and then filtered clear at 65° C. The filtrate is evaporated down to 50% and the residue filtered off at 25° C. (filter material A). The mother liquor is evaporated to dryness. This residue and filter material A are suspended in 2.2 l ethanol and dissolved under reflux with the addition of 30 ml water. Cooling overnight to 25° C., filtration, and drying at 65° C. until constancy of weight is achieved result in 4-(4-methylpiperazin-1-ylmethyl)-N-[4-methyl-3-(4-pyridin-3-yl)pyrimidin-2-ylamino) phenyl]benzamide as light beige, crystalline mesylate (α-crystal form).

Example 2

Preparation of β-Crystal form of 4-(4-methylpiperazin-1-ylmethyl)-N-[4-methyl-3-(4-pyridin-3-yl)pyrimidin-2-ylamino)phenyl]benzamide methanesulfonate—Variant 2

50.0 g (101 mmol) 4-[(4-methyl-1-piperazinyl)methyl]-N-[4-methyl-3-[[4-(3-pyridinyl)-2-pyrimidinyl]amino]phenyl]benzamide is suspended in methanol (480 ml). 9.71 g (101 mmol) methanesulfonic acid and methanol (20 ml) is added, heated to 50° C., activated carbon (5.0 g) added, and the mixture boiled under reflux for 30 minutes, filtered, and concentrated by evaporation. The residue is dissolved in methanol (150 ml) and inoculated with 4-[(4-methyl-1-piperazinyl)methyl]-N-[4-methyl-3-[[4-(3-pyridinyl)-2-pyrimidinyl]amino]phenyl]-benzamide methanesulfonate (β-modification, a few mg), leading to crystallisation of the product. Drying at 50 mbar and 60° C. leads to 4-[(4-methyl-1-piperazinyl)methyl]-N-[4-methyl-3-[[4-(3-pyridinyl)-2-pyrimidinyl]amino]phenyl]benzamide methanesulfonate, β-modification; $R_f$=0.58 (methylene chloride:ethyl acetate:methanol: concentrated aqueous ammonium hydroxide solution=60:10:30:2); HPLC: $t_{ret}$=10.2 min.

Example 3

Preparation of β-crystal form of 4-(4-methylpiperazin-1-ylmethyl)-N-[4-methyl-3-(4-pyridin-3-yl)pyrimidin-3-ylamino)phenyl]benzamide methanesulfonate—Variant 3

670 g (1136 mmol) 4-[(4-methyl-1-piperazin-1-yl)methyl]-N-[4-methyl-3-[[4-(3-pyridinyl)-2-pyrimidinyl]amino]phenyl]benzamide, α-modification, is heated in methanol (1680 ml). The solution is inoculated at 60° C. with 4-[(4-methyl-1-piperazin-1-yl)methyl]-N-[4-methyl-3-[[4-(3-pyridinyl-2-pyrimidinyl]amino]phenyl]benzamide methanesulfonate (β-modification, 55 mg), whereupon the product starts to crystallise. Drying at 50 mbar and 100° C. leads to 4-[(4-methyl-1-piperazinyl)methyl]-N-[4-methyl-3-[[4-(3-pyridinyl)-2-pyrimidinyl]amino]phenyl]-benzamide methanesulfonate, β-modification; $R_f$=0.58 (methylene chloride:ethyl acetate:methanol: concentrated aqueous ammonium hydroxide solution=60:10:30:2); HPLC: $t_{ret}$=10.2 min.

Example 4

Tablets with 4-[(4-methyl-1-piperazin-1-ylmethyl)-N-[4-methyl-3-[[4-(3-pyridinyl-2-pyrimidinyl]amino]-phenyl]benzamide methanesulfonate, β-Crystal form Tablets containing 100 mg of the active substance named in the title are usually prepared in the following composition:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Preparation: The active substance is mixed with carrier materials and compressed on a tableting machine (Korsch EKO, punch diameter 10 mm).

Avicel is microcrystalline cellulose (FMC, Philadelphia, USA).

PVPPXL is polyvinylpolypyrrolidone, cross-linked (BASF, Germany).

Aerosil is silicon dioxide (Degussa, Germany).

Example 6

Capsules with 4-[(4-methyl-1-piperazin-1-ylmethyl)-N-[4-methyl-3-[[4-(3-pridinyl)-2-pyrimidinyl]amino]phenyl]benzamide methanesulfonate, β-Crystal form Capsules containing 100 mg of the compound named in the title as active substance are usually prepared in the following composition:

| Composition | |
|---|---|
| Active ingredient | 100 mg |
| Avicel | 200 mg |
| PVPPXL | 15 mg |
| Aerosil | 2 mg |
| Magnesium stearate | 1.5 mg |
| | 318.5 mg |

The capsules are prepared by mixing the components and filling the mixture into hard gelatin capsules, size 1.

What is claimed is:

1. A crystalline form of the monomethanesulfonic acid addition salt of a compound of formula I,

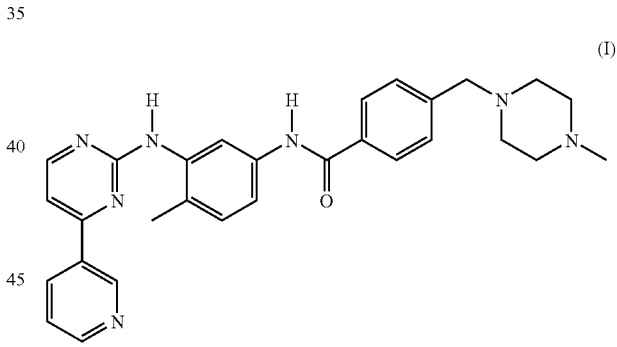

(I)

having non-needle-shaped crystals.

2. A crystalline form according to claim 1 of the methanesulfonic acid addition salt of a compound of formula I, which comprises at least 95% by weight crystals of the β-modification.

3. A crystalline form according to claim 1 of the methanesulfonic acid addition salt of a compound of formula I, which shows on X-ray diffraction a peak at an angle of refraction 2theta of 20°, said peak having a relative line intensity of about 65% as compared to the most intense line in the diagram.

4. A pharmaceutical composition, comprising the crystal form according to claim 1 of the methanesulfonic acid addition salt of a compound of formula I and a pharmaceutically acceptable carrier.

* * * * *